US006448002B1

(12) United States Patent
Hillebrand et al.

(10) Patent No.: US 6,448,002 B1
(45) Date of Patent: Sep. 10, 2002

(54) METHOD TO DETECT CLINICALLY RELEVANT MUTATIONS OF THE DNA SEQUENCE OF KI-RAS ONCOGENE, ITS USE AND A TESTKIT FOR EARLY DIAGNOSIS OF TUMORS

(75) Inventors: Timo Hillebrand; Hans-Christoph Berndt; Peter Bendzko, all of Berlin (DE)

(73) Assignee: Invitek GmbH (DE)

( * ) Notice: Subject to any disclaimer, the term of this patent is extended or adjusted under 35 U.S.C. 154(b) by 0 days.

(21) Appl. No.: 09/242,937

(22) PCT Filed: Aug. 26, 1997

(86) PCT No.: PCT/DE97/01894

§ 371 (c)(1),
(2), (4) Date: May 14, 1999

(87) PCT Pub. No.: WO98/08971

PCT Pub. Date: Mar. 5, 1998

(30) Foreign Application Priority Data

Aug. 26, 1996 (DE) .......................................... 196 35 609

(51) Int. Cl.⁷ .......................... C12Q 1/68; C07H 21/04; B01J 20/02; C12M 1/34; A61K 9/14
(52) U.S. Cl. ..................... 435/6; 435/287.2; 435/288.4; 435/288.7; 435/325; 435/810; 536/24.31; 536/24.33; 536/25.4; 424/489; 502/416
(58) Field of Search .......................... 435/6, 325, 287.2, 435/288.4, 288.7, 810; 536/24.31, 24.33, 25.4, 23.5; 424/489; 502/416

(56) References Cited

U.S. PATENT DOCUMENTS 5,591,582 A * 1/1997 Bos et al. ....................... 435/6
6,017,699 A * 1/2000 Jordan ............................ 435/6
6,037,465 A * 3/2000 Hillebrand et al. ...... 536/25.42

FOREIGN PATENT DOCUMENTS

WO    0 535 376 A1 * 8/1992
WO    95/34569 * 12/1995

OTHER PUBLICATIONS

Wilde, J. et al. J. Clin. Microbiol. 28(6):1300–1307, Jun. 1990.*
Sidransky, D. et al. Science 256:102–105, Apr. 1992.*
Berndt, C. et al. Eur. J. Clin. Chem. Clin. Biochem. 34(10):837–840, Oct. 1996.*
Concepcion Almoguera et al.; Most Human Carcinomas of the Exocrine Pancreas Contain Mutant c–K–ras Genes; Cell. Vol. 53, 549–554, May 20, 1988.
Kathleen Forrester et al.; Detection of High Incidence of K–ras Oncogenes During Human Colon Tumorigenesis; Nature vol. 327, 298–303, May 28, 1987.

* cited by examiner

*Primary Examiner*—W. Gary Jones
*Assistant Examiner*—Diana Johannsen
(74) *Attorney, Agent, or Firm*—Norris, McLaughlin & Marcus P.A.

(57) ABSTRACT

Disclosed is a method to detect clinically relevant mutations of the DNA sequence of the KI-ras oncogene in stool DNA, its use and a testkit based thereon for early diagnosis of tumors, especially tumors of the pancreas and the colon. According to the invention, the method of detection is distinguished by extraction of genomic DNA from stool samples in a series of cleaning operations designed to eliminate inhibitor substances, and by base-complementary hybridization reaction by adding six different oligonucleotides with a defined complementarity to the clinically relevant mutated sequence fragments of the KI-ras gene.

16 Claims, No Drawings

SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
gttggagctc gtggcgta                                              18

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
gttggagctt gtggcgta                                              18

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
gttggagcta gtggcgta                                              18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
gttggagctg ctggcgta                                              18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
gttggagctg atggcgta                                              18

<210> SEQ ID NO 6
<211> LENGTH: 18
<212> TYPE: DNA
<213> ORGANISM: Artificial Sequence
<220> FEATURE:

-continued

```
<223> OTHER INFORMATION: Description of Artificial Sequence:
      oligonucleotide

<400> SEQUENCE: 6
gttggagctg ttggcgta                                                    18
```

METHOD TO DETECT CLINICALLY RELEVANT MUTATIONS OF THE DNA SEQUENCE OF KI-RAS ONCOGENE, ITS USE AND A TESTKIT FOR EARLY DIAGNOSIS OF TUMORS

This application is the national phase of PCT/DE97/01894, filed Aug. 26, 1997.

BACKGROUND OF THE INVENTION

The invention relates to a method for detecting clinically relevant mutations in the DNA sequence of the ki-ras oncogene in DNA, preferably in stool DNA, its use, as well as a test kit for the early diagnosis of tumors, particularly of tumors of the pancreas and the large intestine.

Worldwide, tumors of the large intestine and pancreas are the most frequently occurring cancerous affections and are in third or fourth place in the mortality statistics of malignant growths. Problems of these diseases come to the fore particularly clearly in the case of pancreatic cancer. Because the disease is asymptomatic for a long time, pancreas carcinomas are diagnosed so late, that the average five-year survival rate of patients does not exceed 2% in spite of flawless surgical techniques.

At the present time, there are no satisfactory laboratory parameters for the early diagnosis of pancreatic tumors. For the diagnosis of colorectal carcinoma, the occult blood test is used, for which occult blood is detected in the stool. The analytical reliability of this test is not satisfactory, because occult blood occurs in the stool even in the case of non-malignant diseases, such as hemorrhoids and because positive findings can furthermore also be caused by a large number of interfering stool components, such as peroxidases and catalyses. On the other hand, it is well known that tumors with a diameter of less than 2 cm do not give off sufficient blood to be noticed in an occult blood test method. Even in the case of advanced tumors of the large intestine, the diagnostic sensitivity of the occult blood test is only 50 to 70%.

One possible alternative for the early diagnosis of tumors of the pancreas and the large intestine is offered by the molecular biological detection of relevant mutations in oncogenes, preferably in the ki-ras proto-oncogene. For example, it was possible to show that mutations in the ki-ras proto-oncogene occur in 75 to 90% of pancreatic carcinoma (Almoguera, S., Shiate, D., Forrester, K., Martin, J., Arrheim, N., Perucho, M. (1988) Cell 53, 549–554) as well as in the case of at least 50% of colorectal carcinoma (Forrester, K., Alomugera, C., Han, K., Grizzle, W. E., Perrucho, M. (1987) Nature 327, 298–303).

Until now, the frequency, with which an oncogene has been found for a specific tumor, has been highest in the case of pancreatic carcinoma. Moreover, the relevant mutations are limited to the codons of three amino acids and, in the case of pancreatic carcinoma, to only one amino acid. This fact can simplify the detection of mutations appreciably.

In the case of tumors of the large intestine, as well as in the case of pancreatic tumors, the possibility exists of a non-invasive detection of the oncogene status in the stool. Such a detection was shown for the first time in 1992 by Sidransky and fellow workers (Sidransky, D., Tokino, T., Hamilton, S. R., Kinler, K. W., Levin, B., Vogelstein, B. (1992); Science 256, 102–105). The detection is successful because, on the one hand, a sufficient number of epithelial cells of the pancreas and the intestine reach the stool, tumor cells possibly being more stable than normal epithelial cells under the conditions existing in the stool. On the other, bacteria have no gene for ki-ras, so that the diagnosis is not affected by interference of intestinal flora and epithelial cells. Adenoma, up to a size of 1 cc, can be diagnosed by way of the detection of activated ki-ras.

In spite of these advantageous pre-conditions for a laboratory diagnostic application, there is, up to now, no method for detecting ki-ras mutations in stool DNA, which can be used routinely.

The main problem here lies in the enormous difficulty of isolating DNA of adequate quality from stool samples at a justifiable expense. The extraction method, practiced most frequently at the present time, contains a series of purification steps requiring several hours and extends in total to at least one working week.

Further improvements by Caldas and co-workers resulted in a method, which also required several days for its implementation (Caldas, C., Hahn, S. A., Hruban, R. H., Redston, M. S., Yeo, C. J., Kern, S. E. (1994); Cancer Res. 54, 3568–3573).

Stool is a complex mixtures of cells, which have flaked off, microorganisms, undigested food components, mucous materials and coloring matter, as well as of other soluble and insoluble components of the gastrointestinal tract. Such a complex composition causes a large number of inhibitory materials to be present, which are contaminating components of the isolated DNA solution and, as well, are also intercalated directly in the DNA or bound to the DNA and, for this reason, prevent the use of the isolated DNA for further investigations.

SUMMARY OF THE INVENTION

It is therefore an object of the invention to develop a method of detection for a corresponding gene diagnosis system, which can be used routinely, a suitable method for extracting DNA having a key function for establishing a routinely useful ki-ras test, which can also be automated, as well as to make available a test kit based on the method.

This objective is realized in accordance with claims 1 to 15. Pursuant to the invention, it is accomplished owing to the fact that genomic DNA is extracted by means of multiple purification steps from material samples, preferably from stool samples, all inhibitory materials being eliminated in a highly selective manner, so that the isolated genomic DNA is available without problems for further applications.

Starting materials, within the sense of the invention, are stool samples, biopsy samples from gastrointestinal polyps after endoscopic removal, ercp fluids from the pancreas, sputum and optionally also blood, plasma, serum and urine.

Especially stool samples are incubated pursuant to the invention in a first step with materials, which have absorbing properties, for removing inhibitory materials. The cells, contained in the samples, are lysed with a buffer, which contains chaotropic salts. The genomic DNA, which is subsequently bound to a mineral carrier material, is purified further in a further washing process and then dissolved off from the carrier material by means of a buffer of low ionic strength. In a subsequent purification step, the material or materials (inhibitors), bound in or to the DNA, are then also removed. Especially these materials, bound in or to the DNA, represent potent inhibitors. These are displaced from the DNA by incubation of the already isolated DNA with a buffer, which has an ionic strength greater than 4M and contains a chaotropic salt, such as sodium iodide. A subsequent addition of the carrier material for binding the DNA once again, followed by washing and elution of the DNA, form the conclusion of the purification process. The DNA, isolated in this manner from the samples, is now available for further molecular biological diagnostic techniques.

DESCRIPTION OF THE PREFERRED EMBODIMENTS

In particular, the following purification steps are carried our pursuant to the invention:

a) optionally incubating with preferably chromatographic materials with absorption properties, preferably with a solution of activated charcoal, for the removal of inhibitory materials when a stool sample is used;

b) lysis of the cells, contained in the material samples, with a buffer, which contains chaotropic salts, such as guanidine isothiocyanate, guanidine hydrochloride, lithium chloride or lithium chloride/urea mixtures with an ionic strength greater than 4M;

c) incubation of the lysate with a mineral carrier material for binding the DNA; the carrier material preferably is a highly disperse, non-porous silica with a particle size of 7 nm to 1 $\mu$m and preferably of 40 nm and with a specific surface area of 10 to 300 $m^2/g$ and preferably of 50 $m^2/g$;

d) separation of the carrier material from the lysate by centrifugation;

e) washing the DNA, bound to the carrier material, preferably with a buffer consisting of 50 mM NaCl, 10 mM tris HCl and 1 mM EDTA as well as 70% by volume of ethanol, and removing the DNA by incubating the carrier material with a buffer of low ionic strength, preferably containing 10 mM tris HCl, 0.1 mM EDTA, at a temperature of 48° to 65° C.;

f) incubation of the genomic DNA removed with a buffer, which contains a chaotropic salt, preferably sodium iodide, sodium perchlorate or potassium iodide with ionic strengths greater than 4M by shaking continuously, preferably with 5M sodium iodide for removing substances bound to the DNA from the genomic DNA, g) incubation of the buffer solution with the genomic DNA once again with a mineral carrier material, preferably of highly disperse, nonporous silica particles with a particle size of 7 nm to 1 $\mu$m and preferably of 40 nm and having a specific surface area of 10 to 300 $m^2/g$ and preferably of 50 $m^2/g$, h) separating the solution from the mineral carrier material by centrifugation, i) washing the carrier material with the bound DNA, preferably with a buffer consisting of 50 mM NaCl, 10 mM tris HCl and 1 mM EDTA as well as 70% by volume of ethanol, and once again removing the bound genomic DNA with a buffer of low ionic strength, preferably with 10 mM tris HCl, 0.1 mM EDTA at a temperature of 48° to 65° C.

Pursuant to the invention, the inventive extraction procedure is carried out preferably as a batch method or as a column chromatographic method or as a chromatographic method in a microtiter plate format.

The whole of the extraction procedure requires less than 2 hours for at least 10 different samples and, with that, for the first time solves the problem of extracting genomic DNA from stool samples and other materials in a most ideal manner. The invention permits DNA to be isolated from flaked-off cells of stool samples in an extremely short time.

Surprisingly, by the preferred use of a solution of activated charcoal in the inventive purification method, it was possible to eliminate inhibitory materials, which are not bound directly to the genomic DNA.

Pursuant to the invention, clinically relevant mutations in the DNA sequence of the ki-ras gene are detected subsequently by way of base-complementary hybridization reactions according to well-known techniques with at least 6 different oligonucleotides, with a defined complementarity to possibly mutatively changed sequence sections of the ki-ras gene.

After the extraction of the genomic DNA from the clinical sample has been concluded, the preparation of the ki-ras sequence, which is to be analyzed, follows.

The oligonucleotides and the sections of the ki-ras gene, the sequence of which is mutated and which are to be detected, are incubated, either the oligonucleotides or the sections of ki-ras gene of mutated sequence, which are to be detected, are labeled and the hybridization results are detected by way of the labeling or other methods, known for duplex DNA, are used to detect the hybridization result.

For this purpose, the oligonucleotides and/or the sections of ki-ras gene of mutated sequence or the hybridized DNA are on a solid phase, which preferably is a microtiter plate, an optical waveguide or a silicon chip, a microtiter plate being particularly preferred.

The amplification reaction takes place with a primer pair, one of the primers being coupled at its 5' position with a labeling, preferably a biotin labeling. The DNA fragment, generated after a replication reaction, is also labeled thereby. This labeling subsequently enables the amplified ki-ras fragment to be coupled in a preferred variation of the method to the surface of a solid phase, which is coated with streptavidin and preferably to the surface of a microtest plate over a streptavidin-biotin bridge.

The double-stranded fragment, bound to the surface, is converted into a single strand by addition of a known denaturing solution, such as a sodium hydroxide solution. After the denaturing solution is removed by suction, only the DNA strand, fixed over the biotin-streptavidin bridge, remains on the surface of the microtest plate. This strand thus is the material to be analyzed and corresponds to the ki-ras section, which is to be investigated for the presence of single base mutations. The single ki-ras strand, which is fixed to the plate, is incubated in the following steps with allele-specific oligonucleotides (hybridization probes) under a standard hybridization buffer. The oligonucleotides correspond in each case to a possible ki-ras point mutation or to the ki-ras wild type sequence.

Pursuant to the invention, the oligonucleotides are selected from the point of view of carrying out the hybridization reactions for each of the different allele-specific oligonucleotides under absolutely identical reaction parameters, in order to realize mutation tests simultaneously for different point mutations on one microtest plate.

The six oligonucleotides preferably have the sequences
5'-GTT-GGA-GCT-CGT-GGC-GTA-3' (SEQ. ID NO. 1)
5'-GTT-GGA-GCT-TGT-GGC-GTA-3' (SEQ. ID NO. 2)
5'-GTT-GGA-GCT-AGT-GGC-GTA-3' (SEQ. ID NO. 3)
5'-GTT-GGA-GCT-GCT-GGC-GTA-3' (SEQ. ID NO. 4)
5'-GTT-GGA-GCT-GAT-GGC-GTA-3' (SEQ. ID NO. 5)
5'-GTT-GGA-GCT-GTT-GGC-GTA-3' (SEQ. ID NO. 6)

The decisive step for the detection of a single base mutation consists of highly optimized reaction conditions for essential washing steps after the hybridization reaction is completed. Pursuant to the invention, there are one to five and preferably three washing steps after a 14- to 45-minute and preferably 30-minute incubation time at 38° to 45° C. and preferably at 42° C., in each case for 5 to 15 minutes and preferably 10 minutes, with a washing solution consisting of SDS and SSC at a temperature of 45° to 55° C. and preferably with 0.03% SDS and 0.03% SSC for 10 minutes at a temperature of 50° C. In this connection, it is decisive importance that a hybridization product is retained only if there is complete base complementarity between the ki-ras target and the respective hybridization oligonucleotide. However, each base incomplementarity leads to the selective removal of the oligonucleotide probe.

It was possible to solve these conditions in the inventive method in a most ideal manner. The optimized conditions of the washing steps additionally permit the test for detecting six different ki-ras mutations to be carried out simultaneously on one test plate.

The hybridization results are detected by an indirect enzymatic colorimetric detection, which is well known to those skilled in the art. This detection is based on the fact that hybridization oligonucleotides are provided with a standard labeling, such as digoxigenin or FITC, against which enzyme-conjugated antibodies are used. After addition of a substrate solution, the intensity of the color reaction is determined finally by the measurement transmitted light in a microtest plate reader. This measurement is the parameter for reporting the hybridization result. Standard DNA samples for a ki-ras mutation or for the ki-ras wild type are run at the same time as reference quantities for evaluating the sample analyses.

Preferably, the detection method is carried out in microtiter plates and, with that, has the advantage that the possibility exists of analyzing a large number of different samples, as a result of which it becomes possible to automate the process.

Previously known methods of detecting mutations by way of hybridization reactions are carried out only by means of known techniques of molecular biology, such as dot-blot hybridizations, on filter membranes, for which the hybridization reaction is detected by detecting radioactive labeling. Such a method is extremely time consuming and, due to the use of a method employing radioactivity for the detection, moreover highly dangerous. Likewise, it cannot be automated.

If extraction of the DNA from the samples is included, the inventive method requires about 8 hours. This is a time period, which makes it possible, for the first time, to utilize the ki-ras status in routine laboratory diagnosis as probably the most important clinical parameter for the early diagnosis of malignant mutations, preferably of the colon and the pancreas.

Such a diagnosis will contribute significantly to lowering the mortality rates of these diseases.

The invention moreover relates to a test kit for the detection of mutations in the ki-ras gene. This test kit is characterized by a modular construction and comprises:
1. the DNA extraction system, preferably
   a) a solution of activated charcoal, for removing inhibitory materials when a stool sample is used,
   b) for the lysis of the cells contained in the samples of material, a buffer, which contains chaotropic salts, such as guanidine isothiocyanate, guanidine hydrochloride, lithium chloride or lithium/urea mixtures with ionic strengths greater than 4M; guanidine isocyanate being particularly preferred; DTT, sodium citrate,
   c) for incubating the lysate, a mineral carrier which bonds the DNA; preferably highly disperse, non-porous silica particles with a particle size of 7 nm to 1 $\mu$m and preferably of 40 nm, with a specific surface area of 10 to 300 m$^2$/g and preferably of 50 m$^2$/g,
   d) a washing buffer consisting of 55 mM NaCl, 10 mM tris HCl and 1 mM EDTA as well as 70% by volume of ethanol, and removing the DNA by incubating the carrier material with a buffer of lower ionic strength, preferably with 10 mM tris HCl and 0.1 mM EDTA,
   e) for incubating the removed, genomic DNA, a further buffer, which contains a chaotropic salt and preferably is sodium iodide, sodium perchlorate or potassium iodide with ionic strengths greater than 4M and especially 5M sodium iodide,
   i) for washing the carrier material with the bound DNA, preferably a buffer consisting of 50 mM NaCl, 10 mM tris HCl and 1 mM EDTA as well as 70% by volume of ethanol,
2. primer mixes for the selective amplification of the ki-ras target sequence to be investigated,
3. control cell lines of DNA for the amplification of the wild type or the mutation type of a ki-ras cell line,
4. six oligonucleotides probes with the sequences
   5'-GTT-GGA-GCT-CGT-GGC-GTA-3' (SEQ. ID NO. 1)
   5'-GTT-GGA-GCT-TGT-GGC-GTA-3' (SEQ. ID NO. 2)
   5'-GTT-GGA-GCT-AGT-GGC-GTA-3' (SEQ. ID NO. 3)
   5'-GTT-GGA-GCT-GCT-GGC-GTA-3' (SEQ. ID NO. 4)
   5'-GTT-GGA-GCT-GAT-GGC-GTA-3' (SEQ. ID NO. 5)
   5'-GTT-GGA-GCT-GTT-GGC-GTA-3' (SEQ. ID NO. 6)
5. a solid phase, preferably a microtest plate, including reagents required for the plate assay, as described above.

The system is used preferably for the investigation of stool DNA for the early diagnosis of gastrointestinal tumors, especially for the early diagnosis of pre-neoplastic, colorectal, proliferative diseases.

Due to the universality of the DNA extraction method and the modular construction of the test kit, there is also the possibility of investigating other clinically relevant starting materials for ki-ras mutations. At the same time, the detection system always remains constant.

Our own results also brought proof in this manner of ki-ras mutations after DNA extraction from pancreas secretions (ercp samples). For the first time, therefore, the possibility exists of finding patients at risk for pancreas tumors after investigating this sample material. It is well known to those skilled in the art that inflammatory processes of the pancreas (acute or chronic pancreatitides) frequently can degenerate into malignant phenotypes. However, at the time of its detection, an existing tumor of the pancreas can no longer be treated curatively. The detection of mutative changes in the ki-ras gene can thus be used as a decisive parameter for a prognosis in this regard.

The inventive method furthermore is suitable also in an ideal manner for investigating biopsy samples from gastrointestinal polyps after endoscopic removal. With these samples also, potentially existing, possibly malignant mutations can be diagnosed in good time by detecting ki-ras mutations and patients can be classified as risk patients. The formation of a tumor can thus be prevented by the timely surgical removal of the ki-ras-mutated polyps. Up till now, there have not been any such diagnoses because of the absence of a system of detection, which can be used routinely.

Pursuant to the invention, at least six different oligonucleotides, which have a defined complementarity to known mutatively changed sequence sections of the ki-ras gene, are used for investigating the ki-ras target sequence. With that, the possibility exists of detecting unambiguously more than 80% of all ki-ras mutations associated with a malignant phenotype.

Finally, the invention will be described in greater detail by means of an example.

EXAMPLE

Detection of ki-ras Point Mutations in Stool DNA

Transfer approximately 300 to 500 mg of a stool sample to a 2.0 mL Eppendorf reaction vessel. Add 350 $\mu$L of a washing solution (NaCl, tris; EDTA) and swirl.

Centrifuge for 2 minutes at 14,000 rpm and transfer the supernatant into a new 2.0 mL Eppendorf reaction vessel.

Add 250 $\mu$L of a solution of activated charcoal; shake sample for 10 minutes. Centrifuge for 2 minutes at 14,000 rpm and transfer the supernatant into a new 1.5 mL Eppendorf reaction vessel. Centrifuige for 1 minute at 14,000 rpm and transfer the supernatant into a new 2.0 mL Eppendorf reaction vessel.

Add 1 mL of buffer (guanidine isothiocyanate; DTT, sodium citrate) to lyse cells and incubate for 30 minutes at room temperature.

Add 20 $\mu$L of a mineral carrier suspension from highly disperse, non-porous silica particles with a particle size of approximately 40 nm, a specific surface area of approximately 50 m$^2$/g and incubate for 5 minutes at room temperature. Centrifuge for 1 second at 10,000 rpm and carefully remove the supernatant.

Add 1 mL of washing buffer (NaCl, tris, EDTA, ethanol) and resuspend the pellets, centrifuge for 1 second at 10,000 rpm and carefully remove the supernatant. Repeat the washing step twice. Incubate the open reaction vessel briefly at 60° C. until the ethanol is removed completely.

Add 100 $\mu$L of an eluting agent (10 mM tris HCl; 0.1 mM EDTA), resuspend the pellets and incubate the reaction vessel for 5 minutes at 60° C. Centrifuge for 2 minutes at 14,000 rpm and transfer the supernatant into a new 1.5 mL Eppendorf reaction vessel. Mix the isolated DNA with a solution of sodium iodide with light shaking for 5 minutes.

Once again, add 15 $\mu$L of the mineral carrier suspension to the buffer solution with the genomic DNA and incubate for 5 minutes on ice. Centrifuge for 1 second at 10,000 rpm and carefully remove the supernatant.

Add 1 mL of washing buffer and resuspend the pellets. Centrifuge for 1 second at 10,000 rpm and carefully remove the supernatant. Repeat the washing step twice. Incubate the open reaction vessel briefly at 60° C. until the ethanol is removed completely. Add 50 $\mu$L of eluting buffer (10 mM tris HCl; 0.1 mM EDTA), resuspend the pellets and incubate the reaction vessel for 5 minutes at 60° C. Centrifuge for 2 minutes at 14,000 rpm and transfer the supernatant into a new 1.5 mL Eppendorf reaction vessel.

After the DNA has been extracted, 1 to 10 $\mu$L of the DNA are used for the enzymatic replication of the specific target sequence of the ki-ras gene, which is to be investigated, by means of the polymerase chain reaction (PCR).

In a first PCR reaction, the amplification takes place with a primer mix, for which a restriction site is generated during the amplification reaction of ki-ras wild type DNA. On the other hand, in all amplified DNA fragments, which do not conform to the wild type, this restriction site is not incorporated.

After the amplification reaction, the ki-ras wild type is digested using a restriction enzyme.

In a second amplification reaction, 1 to 2 $\mu$L of the restriction formulation are used as a template DNA. At the same time, the undigested, mutated ki-ras fragments are now concentrated selectively. This amplification reaction takes place with a primer pair, for which one primer is labeled with biotin at its 5' position.

After the amplification reaction, 1 to 5 $\mu$L of the amplification product are taken up 420 $\mu$L of a binding buffer (tris; EDTA, NaCl).

In each case, 50 mL of this formulation are transferred to five wells of a microtest plate. These wells are subsequently used for the analysis of the ki-ras fragments for mutative changes.

After a brief incubation, the binding buffer solution is removed by suction, 50 $\mu$L of a denaturing solution (NaOH) are added and the whole is incubated with light shaking, generating now a single strand DNA, against which an in each case sequence-specific hybridization is subsequently carried out. After the removal of the second DNA strand, which is not fixed to the plate surface, with a washing buffer (tris, EDTA, NaCl), each of the seven wells of the microtest plate is wetted with one of the specifically labeled oligonucleotide probes, such as digoxygenin or FITC under a standard hybridizing buffer. After a 30-minute incubation at 42° C., the respective probes are hybridized with the ki-ras fragment bound to the plate surface.

The specificity of the detection is achieved by washing steps, which must be carried out subsequently under highly stringent conditions. These washing steps are carried out with a solution of 0.03% STS; 0.03% SSC at 50° C. for 3×10 minutes. Under these conditions, all probes, which do not have a complete base complementarity with the ki-ras target sequence, are removed.

In the steps that follow, the hybridization results are detected by well-known classical, colorimetric methods using a microtest plate reader. The signal strength measured is used as a criterion for evaluating the detection of a hybridization product and, with that, as proof of the presence of a mutation or of a wild type ki-ras.

What is claimed is:

1. A method for the detection of mutations in the DNA sequence of a ki-ras oncogene in DNA, comprising the steps of
   a) incubating stool samples containing cells with a solution of activated charcoal to isolate the cells,
   b) lysing the cells with a buffer solution, wherein the buffer solution contains at least one chaotropic salt, to obtain a lysate; containing DNA,
   c) incubating the lysate in a washing buffer with a mineral carrier for binding the DNA to isolate the DNA from the lysate,
   d) separating the mineral carrier from the lysate by centrifugation,
   e) washing the DNA, which is bound to the mineral carrier,
   f) extracting the DNA by incubating the mineral carrier with a buffer of a low ionic strength,
   g) purifying the DNA with the buffer solution containing at least one chaotropic salt,
   h) incubating the buffer solution of g) containing the DNA with the mineral carrier to bind the DNA,
   i) separating the buffer solution of h from the mineral carrier by centrifuging,
   j) washing the mineral carrier to which the DNA is bound in the washing buffer,
   k) eluting the DNA from the mineral carrier with a second buffer of low ionic strength,
   l) amplifying the DNA with a primer pair and coupling the amplification reaction product to a solid phase,
   m) incubating the amplification reaction product with oligonucleotides that detect mutations of th ki-rass oncigene.
   n) hybridizing the amplification reaction product to the oligonucleotides, thereby detecting mutations in the DNA sequence of a ki-ras oncogene in the DNA.

2. The method of claim 1, wherein
   the at least one chaotropic salt is selected from the group consisting of guanidine isothiocyanate, guanidine hydrochloride, lithium chloride, and lithium chloride/urea mixture, the at least one chaotropic salt having an ionic strength of at least 4M,
   the mineralmineral carrier comprises non-porous silica particles, the particles having a particle size of at least 7 nm and a specific surface area of at least 10 m²/g,
   the washing buffer comprises 50 mM NaCl, 10 mM tris HCl, 1 mM EDTA, and 70% by volume of ethanol,
   the buffer of low ionic strength comprises 10 mM tris HCl and 0.1 mM EDTA, wherein the extracting of f is carried out at a temperature of at least 48° C.,
   and the second buffer of low ionic strength is selected from the group consisting of sodium iodide, sodium perchlorate, and potassium iodide, wherein the ionic strength is at least 4M wherein during the eluting of k and the second buffer is continuously shaken.

3. The method of claim 2, wherein the particle size is 40 nm with a surface area of 50 m²/g.

4. The method of claim 1, wherein the buffer solution containing at least one chaotropic salt for lysing the cells contains guanidine isothiocyanate, DTT, and sodium citrate.

5. The method of claim 1, wherein the oligonucleotides are one or more oligonucleotides chosen from the group consisting of:
   5'-GTT-GGA-GCT-CGT-GGC-GTA-3' (SEQ. ID NO. 1)
   5'-GTT-GGA-GCT-TGT-GGC-GTA-3' (SEQ. ID NO. 2)
   5'-GTT-GGA-GCT-AGT-GGC-GTA-3' (SEQ. ID NO. 3)
   5'-GTT-GGA-GCT-GCT-GGC-GTA-3' (SEQ. ID NO. 4)
   5'-GTT-GGA-GCT-GAT-GGC-GTA-3' (SEQ. ID NO. 5) and
   5'-GTT-GGA-GCT-GTT-GGC-GTA-3' (SEQ. ID NO. 6).

6. The method of claim 1, wherein the oligonucleotides are located on the solid phase.

7. The method of claim 1, wherein the solid phase is selected from the group consisting of a microtiter plate coated with streptavidin, an optical waveguide, and a silicon chip.

8. The method of claim 1, wherein during said incubation the amplification reaction product is incubated with the oligonucleotides for at least 15 minutes at a temperature of at least 38° C.

9. The method of claim 8, wherein during said incubating the amplification reaction product is incubated for 30 minutes at a temperature of 42° C., and is washed three times for 10 minutes at 50° C. with a solution of 0.03% SDS and 0.03% SSC.

10. The method of claim 1, wherein the amplification reaction product is coupled to a streptavidin-biotin bridge on the solid phase.

11. The method of claim 1, wherein the buffer solution containing at least one chaotropic salt has an ionic strength of 5M sodium iodide.

12. The method of claim 1, wherein the hybridizing mutations comprises
   a) washing the amplification reaction product at least one time for at least 5 minutes at a temperature of at least 45° C. with a wash solution of SDS and SSC, and
   b) measuring an intensity of transmitted light by calorimetric methods with a microtest plate reader.

13. The method of claim 1, wherein the primer pair is labeled at the 5' position.

14. A kit for detecting mutations in the DNA sequence of the ki-ras oncogene comprising,
   a) a DNA extraction system comprising materials having adsorbing properties to isolate DNA, said DNA extraction system including a plurality of reagents comprising:
      a solution of activated charcoal,
      at least one chaotropic salt selected from the group consisting of guanidine isothiocyante, guanidine hydrochloride, lithium chloride, and lithium chloride/urea mixture, the at least one chaotropic salt having an ionic strength of at least 4M, a mineral carrier comprising non-porous silica particles, the particles having a particle size of at least 7 nm and a specific surface area of at least 10 m²/g, a washing buffer comprising 50 mM NaCl, 10 mM tris HCl, 1 mM EDTA, and 70% ethanol, a buffer of low ionic strength for elution, comprising 10 mM tris HCl and 0.1 mM EDTA, a second buffer containing at least one chaotropic salt having an ionic strength of at least 4M, wherein the at least one chaotropic salt is selected from the group consisting of sodium iodide, sodium perchlorate, and potassium iodide, and a buffer solution for lysing the cells comprising guanidine isothiocyanate, DTT, and sodium citrate, b) primers that selectively amplify a ki-ras sequence, wherein the primers are coupled to a solid phase, c) a ki-ras control cell lines, d) one or more oligonucleotides chosen from the group consisting of:

5'-GTT-GGA-GCT-CGT-GGC-GTA-3' (SEQ. ID NO. 1)

5'-GTT-GGA-GCT-TGT-GGC-GTA-3' (SEQ. ID NO. 2)

5'-GTT-GGA-GCT-AGT-GGC-GTA-3' (SEQ. ID NO. 3)

5'-GTT-GGA-GCT-GCT-GGC-GTA-3' (SEQ. ID NO. 4)

5'-GTT-GGA-GCT-GAT-GGC-GTA-3' (SEQ. ID NO. 5) and

5'-GTT-GGA-GCT-GTT-GGC-GTA-3' (SEQ. ID NO. 6)

e) a solid phase for coupling selected from the group consisting of a microtiter plate coated with streptavidin, an optical waveguide, and a silicon chip, and f) a plurality of reagents comprising a binding buffer comprising tris-HCl, EDTA and NaCl, a washing buffer comprising tris-HCl, EDTA, and NaCl, a denaturing solution of NaOH and a washing solution of SDS and SSC.

15. The kit of claim 14, wherein the solid phase is the microtiter plate coated with streptavidin.

16. The kit of claim 14, wherein the ki-ras controll cell line is selected from the group consisting of a wild-type cell line and a mutated cell line.

* * * * *